United States Patent [19]

Oshiyama

[11] Patent Number: 5,058,661
[45] Date of Patent: Oct. 22, 1991

[54] HEAT EXCHANGER WITH LEAKAGE COLLECTOR

[75] Inventor: Hiroaki Oshiyama, Fuji, Japan

[73] Assignee: Terumo Kabushiki Kaisha, Tokyo, Japan

[21] Appl. No.: 209,532

[22] Filed: Jun. 21, 1988

[30] Foreign Application Priority Data

Jun. 29, 1987 [JP] Japan .................. 62-161905

[51] Int. Cl.[5] .......... F28F 21/06; F28F 9/02; A61M 1/16; A61M 1/36
[52] U.S. Cl. ...................... 165/70; 165/46; 165/158; 165/905; 165/11.1; 210/85; 210/321.8; 261/DIG. 28; 422/46; 422/48
[58] Field of Search ............ 165/70, 46, 158, 905, 165/11.1; 210/85, 321.8; 422/46, 48; 261/DIG. 28

[56] References Cited

U.S. PATENT DOCUMENTS

| | | | |
|---|---|---|---|
| 1,780,837 | 11/1930 | Nott | 165/70 |
| 1,790,151 | 1/1931 | How | 165/70 |
| 1,810,286 | 6/1931 | MacPhee | 165/70 |
| 1,811,402 | 6/1931 | McNeal | 165/70 |
| 2,031,425 | 2/1936 | Muhleisen | 165/70 |
| 2,127,129 | 8/1938 | McNeal | 165/70 |
| 2,670,185 | 2/1954 | Schorner et al. | 165/70 |
| 4,171,014 | 10/1979 | Straub | 165/70 |
| 4,177,816 | 12/1979 | Torgeson | 165/172 |
| 4,480,683 | 11/1984 | Wollbeck et al. | 165/70 |

FOREIGN PATENT DOCUMENTS 0081118 6/1983 European Pat. Off. .
0183250 6/1986 European Pat. Off. .
967162 10/1957 Fed. Rep. of Germany .

Primary Examiner—John Ford
Attorney, Agent, or Firm—Frishauf, Holtz, Goodman & Woodward

[57] ABSTRACT

A heat or material exchanger is provided which comprises a cylindrical housing having a first fluid inlet and a first fluid outlet, an assembly of heat or material-exchange tubes in the housing, partitions securing the opposed ends of the assembly to the housing in a fluid tight seal to partition the housing interior into a first fluid chamber in fluid communication with the first fluid inlet and the first fluid outlet and a second fluid chamber defined in the assembly, a second fluid inlet and a second fluid outlet in fluid communication with the second fluid chamber, an independent spaced defined by the inner wall of the housing and one partition and extending the entire circumference of the housing, but not in fluid communication with the first and second fluid chambers, and a vent in the housing for communicating the space to the ambient atmosphere. When the partition is separated away from the housing, the second fluid enters the space through the gap between the partition and the housing and drains outside through the vent without entering the first fluid chamber. Drainage of second fluid indicates the separation between the partition and the housing.

3 Claims, 3 Drawing Sheets

HEAT EXCHANGER WITH LEAKAGE COLLECTOR

BACKGROUND OF THE INVENTION

This invention relates to a heat or material exchanger for use with blood. More particularly, it relates to an apparatus for carrying out heat or material exchange by passing blood outside a heat or material exchange conduit and passing a heat or material exchange medium inside the conduit, which is suitable for use as a heat exchanger, artificial lung, and artificial kidney.

Prior art known heat exchangers for blood are of the type wherein a heat-exchange tube is received in a housing. The heat-exchange tube is in the form of, for example, a plurality of heat-exchange elongated tubes or a coiled tube. Material exchangers are used as artificial organs such as artificial lungs. They are also of the type wherein a material-exchange tube is received in a housing, the material-exchange tube being in the form of a plurality of gas-exchange hollow fibers for artificial lungs and a plurality of dialysis hollow fibers for artificial kidneys.

Most prior art heat or material-exchange apparatus are of the type wherein blood is passed through the heat or material-exchange tube while heat or material-exchange medium is passed between the tube and the housing. Some of advanced heat or material-exchange apparatus are of the type wherein heat or material-exchange medium is passed through the tube while blood is passed between the tube and the housing. The heat or material-exchange medium used in practice is warm or cool water for heat exchangers, oxygen-containing gas for artificial lungs, and dialysis fluid for artificial kidneys.

In these apparatus, the heat or material-exchange tube or tubes are secured to the housing in a fluid tight seal by applying a potting composition, for example, a polyurethane base potting composition to form a partition.

During the service of these apparatus wherein blood is passed therethrough for heat or material-exchange purpose, there is the risk that the partition would separate from the housing because it can happen that an impact be accidentally applied to the apparatus or the connection between the housing and the partition contain a local area of weak bond. The separation between the partition and the housing is very dangerous because heat or material-exchange fluid can mix with blood after passing through the separated gap or crevice. In addition, it cannot be detected from the outside that blood is contaminated with heat or material-exchange fluid.

SUMMARY OF THE INVENTION

An object of the present invention is to provide a heat exchanger in which heat-exchange fluid does not mix with blood even when the partition is separated from the housing.

Another object of the present invention is to provide a heat exchanger which allows one to readily detect that the partition is separated from the housing.

A further object of the present invention is to provide a material exchanger in which material-exchange fluid does not mix with blood even when the partition is separated from the housing.

A still further object of the present invention is to provide a material exchanger which allows one to readily detect that the partition is separated from the housing.

According to a first aspect of the present invention, there is provided a heat exchanger comprising a generally cylindrical housing having a first fluid inlet and a first fluid outlet, heat-exchange tubular means received in the housing, partitions securing the opposed ends of the heat-exchange tubular means to the housing in a fluid tight seal to partition the housing interior into a first fluid chamber in fluid communication with the first fluid inlet and the first fluid outlet and a second fluid chamber defined in the heat-exchange tubular means, a second fluid inlet and a second fluid outlet in fluid communication with the second fluid chamber, an independent space defined by the inner wall of the housing and the partitions and extending the entire circumference of the housing, but not in fluid communication with the first and second fluid chambers, and a vent in the housing for communicating the space to the ambient atmosphere.

According to a second aspect of the present invention, there is provided a material exchanger comprising a generally cylindrical housing having a first fluid inlet and a first fluid outlet, material-exchange tubular means received in the housing, partitions securing the opposed ends of the material-exchange tubular means to the housing in a fluid tight seal to partition the housing interior into a first fluid chamber in fluid communication with the first fluid inlet and the first fluid outlet and a second fluid chamber defined in the material-exchange tubular means, a second fluid inlet and a second fluid outlet in fluid communication with the second fluid chamber, an independent space defined by the inner wall of the housing and one of the partitions and extending the entire circumference of the housing, but not in fluid communication with the first and second fluid chambers, and a vent in the housing for communicating the space to the ambient atmosphere.

BRIEF DESCRIPTION OF THE DRAWINGS

The above and other objects, features, and advantages of the present invention will be more fully understood by reading the following description taken in conjunction with the accompanying drawings, in which.

DETAILED DESCRIPTION OF THE INVENTION

Figure 1:
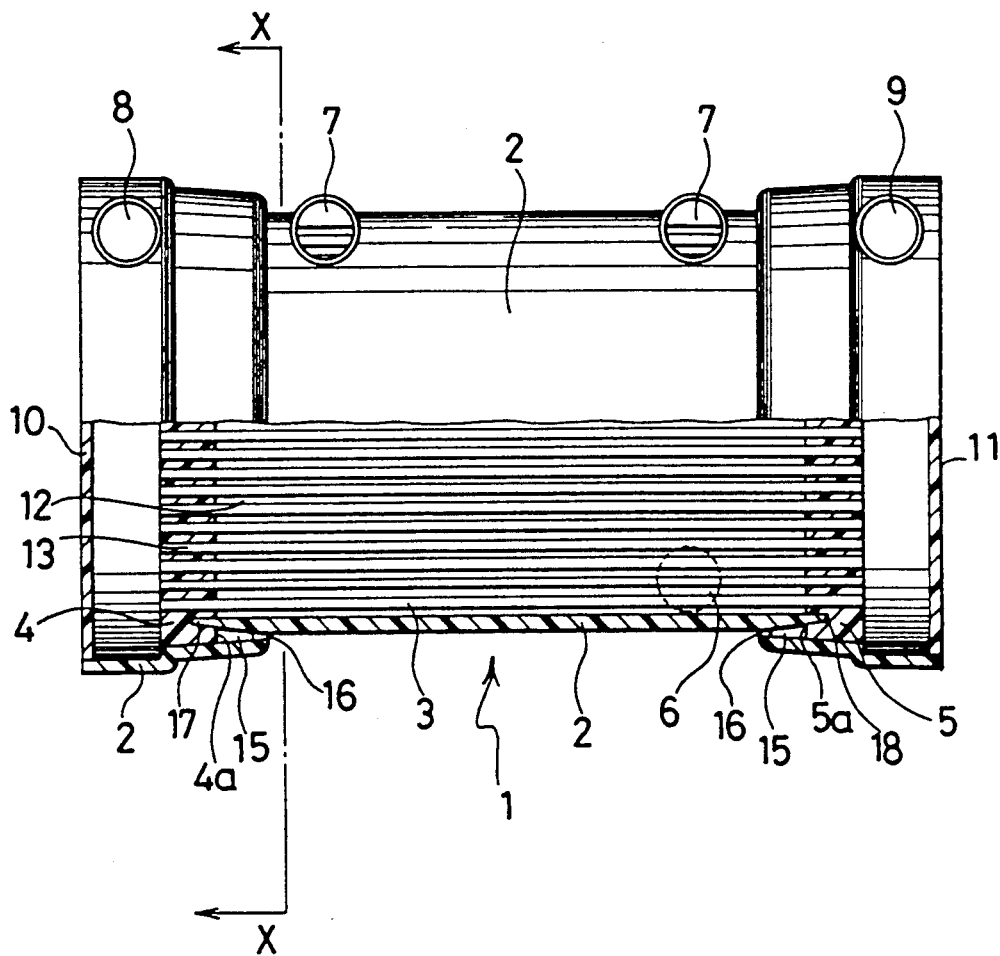
FIG. 1 is a partially cross-sectional side elevation of a heat exchanger according to one embodiment of the present invention.

The heat or material exchanger of the present invention will be described with reference to FIGS. 1 through 3.

The heat or material exchanger generally designated at 1 includes a generally cylindrical housing 2 having a first fluid inlet 6 and a first fluid outlet 7. A heat or material exchange tubular means 3 is received in the housing 2. Circular partitions 4 and 5 are placed in the housing 2 to secure the opposed ends of the exchange tubular means 3 to the housing 2 in a fluid tight sea to partition the housing 2 interior into a first fluid chamber 12 in fluid communication with the first fluid inlet 6 and the first fluid outlet 7 and a second fluid chamber 13 defined in the exchange tubular means 3. More particularly, the first fluid chamber 12 is defined by the inner wall of the housing 2 and the outside wall of the exchange tubular means 3 and delimited by the opposed partitions 4 and 5 so that it is in fluid communication with the first fluid inlet 6 and the first fluid outlet 7. The second fluid chamber 13 is constituted by the interior of the exchange tubular means 3 so that it is in fluid communication with the outsides of the partitions 4 and 5. A second fluid inlet 8 and a second fluid outlet 9 are in fluid communication with the second fluid chamber 13. An independent space 15 is defined by the inner wall of the housing 2 and each of the partitions 4 and 5 and extends the entire circumference of the housing 2, but is not in fluid communication with the first and second fluid chambers 12 and 13. A vent 16 is opened in that portion of the housing 2 enclosing the space 15 for communicating the space 15 to the ambient atmosphere.

Figure 2:
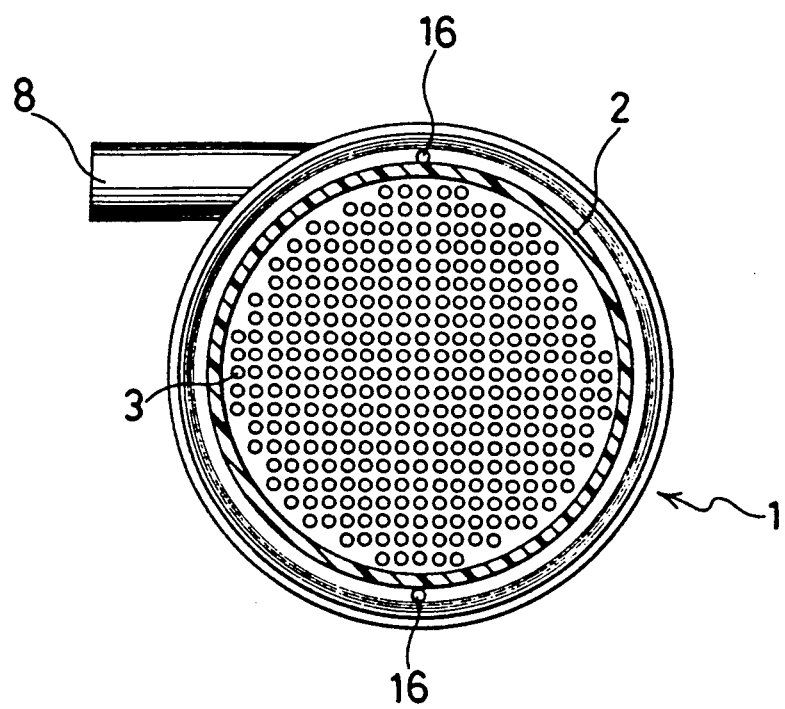
FIG. 2 is a cross section taken along lines X—X in FIG. 1.

The invention will be described in more detail by referring to FIGS. 1 and 2 showing the embodiment in which the apparatus of the present invention is applied to a heat exchanger.

The heat exchanger 1 includes the cylindrical housing 2 defining an interior chamber and having opposed open ends. An assembly 3 of heat-exchange tubes is received in the housing 2. The assembly 3 is formed from a plurality of elongated slender tubes which may be made from metal having a high heat conductivity such as stainless steel, aluminum and copper to have an inner diameter of from about 0.5 to about 10 mm, preferably from about 2 to about 5 mm. For example, about 10 to about 2,000, preferably about 50 to about 1,000 tubes are bundled in a mutually spaced-apart relationship to form the assembly which is axially accommodated in the housing. The heat-exchange tubes are illustrated as straight tubes in the embodiment of FIG. 1, although spiral tubes may also be used. The heat-exchange tubular means used in the present invention is not limited to an assembly of elongated slender tubes, and encompasses a single tube in coil form.

The circular partitions 4 and 5 are transversely placed in the housing 2 to secure the opposed ends of the heat-exchange tube assembly 3 to the housing 2 in a fluid tight seal. The partitions 4 and 5 may be formed from a potting composition based on a polymer such as polyurethane and silicone rubber. The partitions 4 and 5 together with the heat exchange tube assembly 3 partition the housing 2 interior into the first fluid chamber 12 which is a blood chamber and the second fluid chamber 13 which is a heat-exchange fluid chamber in the illustrated embodiment. More particularly, the first fluid chamber 12 is defined by the inner wall of the housing and the outside walls of the heat exchange tubes and delimited by the opposed partitions 4 and 5 so that it is in fluid communication with the first fluid inlet 6 and the first fluid outlet 7. The second fluid chamber 13 is constituted by the lumens of the heat exchange tubes so that it is in fluid communication with the outsides of the partitions. The first fluid inlet 6 in the form of a blood inlet conduit is located at an intermediate lower portion of the housing 2 and extends outward from the outer wall of the housing 2 in a substantially tangential direction. The first fluid outlets 7 in the form of a blood outlet conduit are located at an intermediate upper portion of the housing 2 and extends outward from the outer wall of the housing 2 in a substantially tangential direction.

The housing 2 may be cylindrical or polygonal in configuration. A cylindrical housing is preferred. The housing may be molded from any desired materials, preferably resinous molding materials such as polycarbonate, acryl-styrene copolymers and acryl-butylene-styrene copolymers.

The second fluid inlet 8 which is a heat-exchange fluid inlet conduit is provided to one end portion of the housing 2 that extends beyond the partition 4. The second fluid outlet 9 which is a heat-exchange fluid outlet conduit is provided to the other end portion of the housing 2 that extends beyond the other partition 5. The second fluid inlet and outlet 8 and 9 are in fluid communication with the second fluid chamber 13 which is given by the lumens of the heat-exchange tubes 3.

The housing 2 is closed at both ends by closure members 10 and 11. The closure members 10 and 11 may be a disk having substantially the same contour as the inner cross-sectional shape of the housing 2 and made of, for example, polycarbonate, acryl-styrene copolymers and acryl-butylene-styrene copolymers. The disk 10 and 11 is secured to the end of the housing 2 to form a fluid tight seal by adhesive or solvent bonding or fusion bonding such as dielectric heat sealing, ultrasonic sealing and induction heat sealing. The radially inner wall of the housing 2, the axially outside wall of the partition 4 and the axially inside wall of the closure member 10 define a fluid entrance chamber which is in communication with both the heat-exchange fluid inlet 8 and the heat-exchange fluid chamber 13. Similarly, the inner wall of the housing 2, the outside wall of the partition 5 and the inside wall of the closure member 11 define a fluid exit chamber which is in communication with both the heat-exchange fluid outlet 9 and the heat-exchange fluid chamber 13.

The annular space 15 is defined by the inner wall of the housing 2 and the inside wall of each of the partitions 4 and 5 and extends the entire circumference of the housing 2. The annular space 15 is an independent space because it is not in fluid communication with the first fluid or blood chamber 12 and the second fluid or heat exchange fluid chamber 13 (and hence, the fluid entrance and exit chambers). The vent 16 is opened in that portion of the housing 2 enclosing the space 15 to communicate the space to the ambient atmosphere.

More particularly, that portion of the housing to which the partition 4 or 5 is fused is provided with an annular extension 17 or 18 which axially extends from an intermediate portion of the housing toward the end of the housing. Differently stated, the end portion of the housing is forked into two, an annular end portion and an annular extension radially inside thereof. The partition 4 or 5 is secured to the housing 2 so that the extension 17 or 18 is partially enclosed by the partition. The space 15 is then defined by the radially outer surface of the extension 17 or 18, the radially inner surface of the annular end portion of the housing 2, and the axially inside surface 4a or 5a of the partition 4 or 5 located between the extension 17 or 18 and the annular end portion of the housing 2.

The annular end portion of the housing 2 is perforated with the vent 16 to communicate the space 15 to the ambient atmosphere. It suffices that at least one vent 16 is perforated in the housing end portion defining the space although a plurality of vents may preferably be formed. Two vents 16 are formed in the embodiment of FIG. 2 which is a cross section taken along lines X—X in FIG. 1 while two to sixteen vents are usually formed. The vent 16 may be of any desired size and shape as long as it does not substantially lower the strength of the housing 2. For example, the vent 16 may be a circular cross-section opening having a diameter of from about 1 to about 10 mm. The vent 16 may be formed at any desired location as long as it is in communication with the space 15. Preferably, the vent 16 is located at that portion of the housing which is bottomed during the operation of the heat exchanger because any heat-exchange fluid entering the space 15 can be readily drained therethrough.

The provision of the space 15 and the vent 16 ensures that even when the partition 4 or 5 is separated from the housing 2 at their connection to create a gap, the heat-exchange fluid would pass to the annular space 15 through the gap and then to the outside through the vent 16, preventing the heat-exchange fluid from entering the blood chamber 12.

The end portion of the housing 2 to which the partition is connected is formed as an annular skirt portion which is expanded to have an increased diameter relative to the intermediate portion as shown in FIG. 1. In this case, the annular extension 17 or 18 is an axial extension straight from the intermediate portion. That is, the forked end portion of the housing 2 consists of the skirt portion and the straight extension. The partition 4 or 5 is formed to extend throughout the cross section of the skirt portion such that the extension 17 or 18 is partially enclosed by the partition. The space 15 is defined by the radially outer surface of the extension 17 or 18, the radially inner surface of the annular skirt portion, and the axially inside surface 4a or 5a of the partition 4 or 5 located between the extension 17 or 18 and the angular skirt portion. The axial free end of the extension 17 or 18 is embedded in the partition 4 or 5. The vent 16 is formed in the skirt portion of the housing 2. This design of the housing and partition makes it easy to define the annular space 15. In the preferred embodiment wherein the axial distal end of the extension 17 or 18 is embedded in the partition 4 or 5, when an impact is applied to the heat exchanger during its operation, the impact transmitted to the extension is absorbed by the partition, preventing the distal end of the extension from separating from the partition. Then it is prevented that blood in the blood chamber 12 leaks out of the vent 16 through the space 15.

The housing 2 is provided with the heat-exchange fluid inlet and outlet 8 and 9 in the embodiments illustrated above although the heat exchanger of the present invention is not limited to this structure. It is possible that the partitions be located at the extreme ends of the housing. One end of the housing is covered with a fluid inlet cap having a heat-exchange fluid inlet port to define with the partition an outside chamber in communication with the second fluid chamber 13. The other end of the housing is covered with a fluid outlet cap having a heat-exchange fluid outlet port to define with the other partition another outside chamber in communication with the second fluid chamber 13. These caps may be attached to the housing ends by means of fastener rings, by adhesive bonding or fusion bonding such as dielectric heat sealing and ultrasonic sealing, or by mechanical snug engagement.

The heat exchanger described in the foregoing embodiments is of the type wherein heat-exchange fluid is passed through the interior of the heat-exchange tube assembly and blood is passed through the first fluid chamber defined between the housing and the heat-exchange tube assembly. Conversely, the heat exchanger may be of the type wherein blood is passed through the interior of the heat-exchange tube assembly and heat-exchange fluid is passed through the first fluid chamber defined between the housing and the heat exchange tube assembly. In the latter type, blood flows out of the space through the vent when the partition has separated from the housing to create a gap. It is then easily detectable that any separation has occurred between the partition and the housing. The tubes connected to the heat exchanger are clamped before the heat exchanger is replaced.

Figure 3:
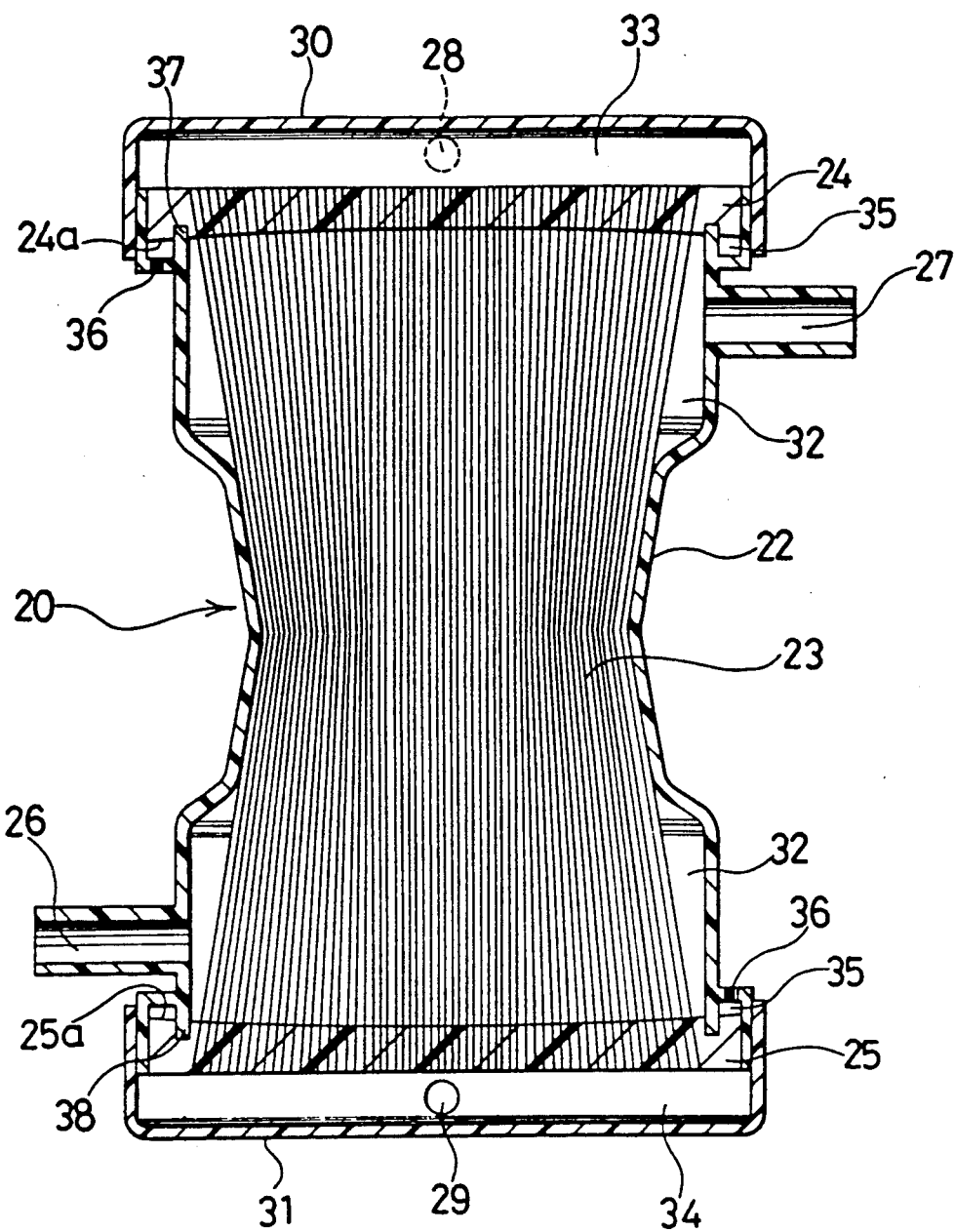
FIG. 3 is a cross-sectional view of a material exchanger according to another embodiment of the present invention.

Another embodiment of the present invention is now described wherein the material exchanger is applied to an artificial lung or oxygenator as shown in FIG. 3.

The artificial lung generally designated at 20 is usually operated in an upright position as shown in FIG. 3. The artificial lung 20 includes a generally cylindrical housing 22 and an assembly of gas-exchange hollow fibers 23 received in the housing. Each of the fibers is a hollow tubular membrane through which material is exchanged. Partitions 24 and 25 are disposed at the open ends of the housing to secure the opposed ends of the hollow fiber assembly to the housing 22 in a liquid tight seal. The interior of the housing 22 is parted by the partitions 24 and 25 into a first fluid or blood chamber 32 which is defined by the inner wall of the housing and the outer walls of the hollow fibers 23 and a second fluid or gas chamber which is constituted by the lumens of the hollow fibers 23. The housing 22 is provided with a first fluid or blood inlet 26 and a first fluid or blood outlet 27 in communication with the blood chamber 32.

The upper end of the housing 22 having the partition 24 secured thereto is covered with a gas entrance cap 30 having a second fluid or gas inlet 28. Between the outside surface of the partition 24 and the inside surface of the gas entrance cap 30 is defined a gas entrance chamber 33 which is in communication with the gas chamber or the lumens of the hollow fibers 23. Similarly, the lower end of the housing 22 having the partition 25 secured thereto is covered with a gas discharge cap 31 having a second fluid or gas outlet 29. Between the outside surface of the partition 25 and the inside surface of the gas discharge cap 31 is defined a gas discharge chamber 34 which is in communication with the gas chamber or the lumens of the hollow fibers 23.

The artificial lung of the type wherein blood is passed outside the hollow fibers has the advantage that blood can be passed through the artificial lung only by gravity drainage from the patient body because blood experiences a less pressure drop across the lung, eliminating the need for a blood feed pump which is otherwise disposed upstream of the lung in a blood circulating circuit.

Each hollow fiber 23 consists of a porous membrane in tubular form having an inner diameter of from about 100 to about 1000 $\mu$m, wall thickness of from about 5 to about 200 $\mu$m, preferably from about 10 to about 100 $\mu$m, and a porosity of from about 20 to about 80%, preferably from about 30 to about 60%, with pores having a diameter of from about 0.01 to about 5 $\mu$m, preferably from about 0.01 to about 1 $\mu$m. The porous membrane is made of hydrophobic polymeric materials such as polypropylene, polyethylene, polysulfone, polyacrylonitrile, polytetrafluoroethylene, and cellulose acetate. The porous membrane is preferably made of polyolefinic resins, and most preferably polypropylene. The membrane is preferably formed from such a resin by a drawing or solid-liquid phase separation technique such that the membrane has pores formed in its wall.

The cylindrical housing 22 is formed from, for example, polycarbonate, acryl-styrene copolymers, or acryl-butylene-styrene copolymers. The housing 22 is preferably cylindrical and transparent because the transparent housing ensures an easy observation of the interior.

Within the housing 22 are received a plurality of, for example, about 5,000 to about 100,000, hollow fibers 23 which axially extend in parallel. The assembly of hollow fibers 23 is secured to the opposed ends of the housing 22 in a liquid tight seal by opposed partitions 24 and 25 such that the opposed ends of the hollow fibers 23 are open outside the partitions 24 and 24. The partitions 24 and 25 are formed of a potting composition based on polyurethane or silicone rubber. The housing 22 interior between the partitions 24 and 25 is divided into a gas chamber defined inside the hollow fibers 23 and a blood chamber 32 defined outside the hollow fibers 23.

The housing 22 at the upper and lower ends is covered with the gas entrance cap 30 having the gas inlet 28 and the gas discharge cap 31 having the gas outlet 29. The caps may be secured to the housing ends by fusion bonding such as ultrasonic sealing, dielectric heat sealing, and induction heat sealing, adhesive bonding, or mechanical engagement. A fastening ring (not shown) may also be used to secure the cap to the housing end.

The lung 20 includes an annular space 35 which is defined by the radially outer area 24a or 25a of the inside wall of the partition 24 or 25 and the inner wall of the housing 22. The annular space 35 is an independent space which is not in communication with the blood chamber 32 and the gas chamber (including the gas entrance and discharge chambers 33 and 34). The housing 22 is formed with a vent 36 to communicate the annular space 35 to the ambient atmosphere.

More particularly, that portion of the housing 22 to which the partition 24 or 25 is fusingly united is provided with an annular extension 37 or 38 which axially extends from an intermediate portion of the housing toward the end of the housing. Differently stated, the end portion of the housing is forked into two, an annular end portion and an annular extension radially inside thereof. The partition 24 or 25 is secured to the housing so that the extension 37 or 38 is partially enclosed by the partition. The space 35 is then defined by the radially outer surface of the extension 37 or 38, the radially inner surface of the annular end portion of the housing 22, and the axially inside surface 24a or 25a of the partition 24 or 25 located between the extension 37 or 38 and the annular end portion of the housing 22. The annular end portion of the housing 22 is perforated with the vent 36 to communicate the space 35 to the ambient atmosphere.

The provision of the space 35 and the vent 36 ensures that even when the partition 24 or 25 is separated from the housing 22 at their connection to create a gap, the oxygen-containing gas from the gas inlet 28 would pass to the annular space 35 through the gap and then to the outside through the vent 36, preventing the oxygen-containing gas from entering the blood chamber 32.

More preferably, the end portion of the housing 22 to which the partition is connected is formed as an annular skirt portion which is expanded to have an increased diameter as compared with the intermediate portion as shown in FIG. 3. In this case, the annular extension 37 or 38 is an axial extension straight from the intermediate portion. That is, the forked end portion of the housing 22 consists of the skirt portion and the straight extension. The partition 24 or 25 is formed to extend throughout the cross section of the skirt portion such that the extension 37 or 38 is partially enclosed by the partition. The space 35 is defined by the radially outer surface of the extension 37 or 38, the radially inner surface of the annular skirt portion, and the axially inside surface 24a or 25a of the partition 24 or 25 located between the extension 37 or 38 and the annular skirt portion. Preferably, the axial free end of the extension 37 or 38 is embedded in the partition 24 or 25. The vent 36 is formed in the skirt portion of the housing 22. This design of the housing and partition makes it easy to define the annular space 35. In the preferred embodiment wherein the axial distal end of the extension 37 or 38 is embedded in the partition 24 or 25, when an impact is applied to the artificial lung during its operation, the impact transmitted to the extension is absorbed by the partition, preventing the distal end of the extension from separating from the partition. Then it is prevented that blood in the blood chamber 32 leaks out of the vent 36 through the space 35.

In the above-mentioned embodiment, the housing of the artificial lung is provided with the annular spaces in association with both the partitions on the gas inlet and outlet sides. However, when the artificial lung is used upright as shown in FIG. 3, an annular space may be formed in association with the top partition and an annular space need not be formed for the bottom partition. Preferably, annular spaces are provided for both the partitions.

The artificial lung of the type wherein gas is passed through the interior of hollow fibers and blood is passed through the first fluid chamber defined between the hollow fibers and the housing is described in the foregoing embodiment. However, the present invention is not limited to this type and may be applied to the type wherein blood is passed through the interior of hollow fibers and gas is passed through the first fluid chamber defined between the hollow fibers and the housing. In the latter type, blood flows out of the space through the vent when the partition has separated from the housing to create a gap. It is then easily detectable that any separation has occurred between the partition and the housing. The tubes connected to the artificial lung are clamped before the lung is replaced.

Although the material exchanger of the present invention is described as being applied to an artificial lung, it is also applicable to other artificial organs such as an artificial kidney. When the material exchanger of the present invention is applied to an artificial kidney, the material-exchange tubes are dialysis hollow fibers which may be hollow fibers of regenerated cellulose (such as cuprammonium cellulose and acetate cellulose) and polyvinyl alcohol. The shape and structure of the remaining apparatus are approximately the same as the artificial lung embodiment.

The heat or material exchanger of the present invention is set in an extracorporeal circuit. For example, in a circuit having a heat exchanger (as shown in FIG. 1) incorporated therein, blood enters the heat exchanger from the blood inlet 6 and passes through the blood chamber 12 defined between the housing 2 and the heat-exchange tubes 3 while the heat exchange fluid enters the heat exchanger from the fluid inlet 8 and passes through the lumens of the heat-exchange tubes 3. As blood passes through the blood chamber 12, it comes in contact with the heat-exchange tubes 3 and is heated or cooled therewith depending on the temperature of the fluid passing the tubes 3. The heated or cooled blood then exits the heat exchanger from the blood outlet 7. In general, blood is passed through the heat exchanger at a flow rate of about 1 to about 6 liters per minute while the heat-exchange fluid, usually warm or cool water, is passed at a flow rate of from about 5 to about 20 liters per minute. The heat-exchange fluid side is under a higher pressure.

The heat exchanger is provided with the annular space 15 which is defined between the radially outer area 4a, 5a of the inside wall of the partition 4, 5 and the inner wall of the housing 2 and out of communication with the blood chamber 12, and the vent 16 for communicating the space 15 to the ambient atmosphere. Even when the partition 4 or 5 is disconnected from the housing 2, the heat-exchange fluid enters the annular space 15 through the gap between the partition 4 or 5 and the housing 2 and then drains out through the vent 16 without entering the blood chamber 12. Since any disconnection between the partition 4 or 5 and the housing 2 can be readily detected, the heat exchanger can be replaced in time.

Where the material exchanger is an artificial lung as shown in FIG. 3, blood enters the lung from the blood inlet 26 and passes through the blood chamber 32 defined between the housing 22 and the gas-exchange hollow fibers 23 while oxygen containing gas enters the lung from the gas inlet 28 and passes through the lumens of the hollow fibers 23. As blood passes through the blood chamber 32, it comes in contact with the gas-exchange hollow fibers 23 through which carbon dioxide is removed from and oxygen is added to the blood. The oxygenated blood then exits the lung from the blood outlet 27.

The lung 20 is provided with the annular space 35 which is defined between the radially outer area 24a, 25a of the inside wall of the partition 24, 25 and the inner wall of the housing 22 and out of communication with the blood chamber 32, and the vent 36 for communicating the space 35 to the ambient atmosphere. Even when the partition 24 or 25 is disconnected from the housing 22, the oxygen containing gas enters the annular space 35 through the gap between the partition 24 or 25 and the housing 22 and then drains out through the vent 36 without entering the blood chamber 32. Since any disconnection between the partition 24 or 25 and the housing 22 can be readily detected, the lung can be replaced in time.

BENEFITS OF THE INVENTION

With the heat or material exchanger of the above-illustrated structure, even when the partition is separated from the housing to form a gap or crevice therebetween, the second fluid enters the annular space through the gap and drains outside through the vent. The heat exchanger is operated safely without the risk of the second fluid entering the first fluid chamber. Drainage of the second fluid leads to a quick detection of the separation between the partition and the housing.

The preferred embodiment wherein the end portion of the housing is forked into an annular skirt portion having an increased diameter and an annular extension has the advantages that the annular space can be readily defined by the outer surface of the extension, the inner surface of the skirt portion, and the inside surface of the partition between the extension and the skirt portion of the housing. Preferably, the distal end of the extension is embedded in the partition. Even when any accidental impact is applied to the housing, a component of the impact transmitted to the extension is absorbed by the partition, eliminating the risk of the extension separating from the partition.

I claim:
1. A heat exchanger comprising:
a generally cylindrical housing having:
   a interior;
   a circumference;
   first and second end portions;
   a blood inlet;
   a blood outlet; and
   a pair of annular extensions, which respectively extend inside a different one of said first and second end portions of said housing;
heat exchange tubular means positioned in said housing, said heat exchange tubular means having first and second end portions;
a pair of partitions formed from a potting composition securing said first and said second end portions, respectively, of said heat exchange tubular means to said housing in a fluid tight seal, said partitions partitioning said interior of said housing into:
   a blood chamber which is in fluid communication with said blood inlet and said blood outlet; and
   a heat exchange fluid chamber defined in said heat exchange tubular means;
said annular extension having ends which extend, respectively, into said first and second end portions, said ends being embedded in said potting compound forming said partitions;
a heat exchange fluid inlet;
a heat exchange fluid outlet;
said heat exchange fluid inlet and said heat exchange fluid outlet being in fluid communication with said heat exchange fluid chamber;
first and second cavities formed respectively at each of said first and second end portions of said housing, each cavity being defined by one of said pair of annular extensions, one of said first and second end portions of said housing, and one of said pair of partitions;
each of said cavities extending around said circumference of said housing out of fluid communication with said blood and heat exchange fluid chambers; and
apertures formed in said housing for venting each of said first and second cavities to ambient atmospheric pressure.

2. The heat exchanger according to claim 1, wherein each of said first and second end portions of said housing comprises an annular skirt having:
   an outer diameter; and
   an intermediate portion which has a preselected diameter smaller than said outer diameter;
   each of said annular skirts, respectively, encircling a different one of said partitions;

each of said pair of annular extensions of said housing respectively extending inside a different one of said annular skirts; and each of said pair of partitions respectively being secured to a different one of said annular skirts and sealingly embedding therein said pair of annular extensions extending respectively into said annular skirts.

3. The heat exchanger of claim 1 wherein said heat-exchange tubular means comprises a plurality of heat-exchange elongated tubes.

* * * * *